United States Patent
Lin et al.

(10) Patent No.: US 11,230,529 B2
(45) Date of Patent: Jan. 25, 2022

(54) METHOD OF PREPARING 3-FLUOROALKYL-1 SUBSTITUTED PYRAZOL-4-CARBOXYLIC ACID BY AIR OXIDATION

(71) Applicant: (ABA CHEMICALS (NANTONG) LIMITED), Jiangsu (CN)

(72) Inventors: Zhigang Lin, Shanghai (CN); Yueheng Jiang, Shanghai (CN); Tong Cai, Shanghai (CN)

(73) Assignee: ABA CHEMICALS (NANTONG) LIMITED, Jiangsu (CN)

( * ) Notice: Subject to any disclaimer, the term of this patent is extended or adjusted under 35 U.S.C. 154(b) by 0 days.

(21) Appl. No.: 15/328,482

(22) PCT Filed: Feb. 19, 2014

(86) PCT No.: PCT/CN2014/000163
§ 371 (c)(1),
(2) Date: Jan. 23, 2017

(87) PCT Pub. No.: WO2015/109420
PCT Pub. Date: Jul. 30, 2015

(65) Prior Publication Data
US 2017/0217900 A1 Aug. 3, 2017

(30) Foreign Application Priority Data

Jan. 21, 2014 (CN) .......................... 201410025966.0

(51) Int. Cl.
*C07D 231/14* (2006.01)
*C07D 231/16* (2006.01)

(52) U.S. Cl.
CPC ......... *C07D 231/14* (2013.01); *C07D 231/16* (2013.01)

(58) Field of Classification Search
CPC .................................................. C07D 231/14
See application file for complete search history.

(56) References Cited

FOREIGN PATENT DOCUMENTS

| CN | 1447798 | A | 10/2003 |
| CN | 101687806 | A | 3/2010 |
| JP | 2010202649 | A | 9/2010 |
| WO | WO 2009/000441 | A1 * | 12/2008 |
| WO | 2012065932 | A1 | 5/2012 |

* cited by examiner

*Primary Examiner* — Shawquia Jackson
(74) *Attorney, Agent, or Firm* — Proi Intellectual Property US; Klaus Michael Schmid

(57) ABSTRACT

Provided is a method of preparing 3-fluoroalkyl-1-substituted pyrazol-4-carboxylic acid by air oxidation. The methoduses 3-fluoroalkyl-1-substituted pyrazol-4-formaldehyde as raw material for reaction in a neutral or alkaline condition under the action of a catalyst and with air as an oxidizing agent, to obtain 3-fluoroalkyl-1-substituted pyrazol-4-carboxylic acid. The method employs a mild, safe and clean reaction, and is suitable for industrial mass production.

4 Claims, No Drawings

METHOD OF PREPARING 3-FLUOROALKYL-1 SUBSTITUTED PYRAZOL-4-CARBOXYLIC ACID BY AIR OXIDATION

TECHNICAL FIELD

The Invention relates to the field of chemical production technology, particularly to a method of preparing 3-fluoroalkyl-1-substituted pyrazol-4-carboxylic acid by air oxidation.

BACKGROUND ART 3-fluoroalkyl-1-substituted pyrazol-4-carboxylic acid is the important intermediate of some new pesticides, such as Isopyrazam (CAS: 881685-58-1), Sedaxane (CAS: 874967-67-6) and Penthiopyrad (CAS: 18367 5-82-3). Therefore, we research and develop its preparing method.

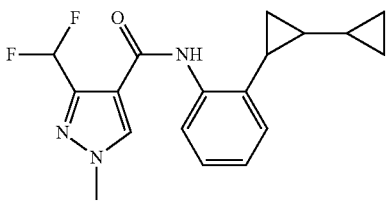

874967-67-6

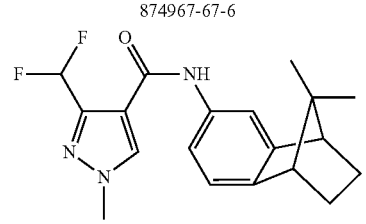

881685-58-1

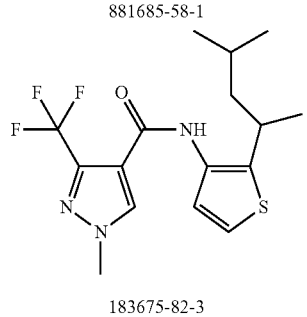

183675-82-3

In the literature, 3-fluoroalkyl-1-substituted pyrazol-4-formaldehyde is oxidized to obtain oxidizing agents of 3-fluoroalkyl-1-substituted pyrazol-4-carboxylic acid, mainly including potassium permanganate (JP2010202649; U.S. Pat. No. 6,063,734, etc.) and PCC/periodic acid (WO 2010130767; WO 2011061205, etc.); and sodium hydroxide/hydrogen peroxide (WO 2012065944; WO 2011151 383, etc.) is in common use. Potassium permanganate and PCC are liable to cause environmental contamination. As for hydrogen peroxide, the feature of instability makes very slow reaction at low reaction temperature and severe decomposition at high reaction temperature, leading to potential safety hazard. Therefore, we study and invent the new method to catalyze air oxidation.

SUMMARY OF THE INVENTION

The Invention provides a new method of preparing 3-fluoroalkyl-1-substituted pyrazol-4-carboxylic acid by air oxidation, which employs a mild, safe and clean reaction and is suitable for industrial mass production.

The technical solution of the Invention employed is:

A method of preparing 3-fluoroalkyl-1-substituted pyrazol-4-carboxylic acid by air oxidation, characterized in that 3-fluoroalkyl-1-substituted pyrazol-4-carboxylic acid (Equation II) is obtained with 3-fluoroalkyl-1-substituted pyrazol-4-formaldehyde (Equation I) as raw material for reaction in a neutral or alkaline condition under the action of a catalyst and with the air as an oxidizing agent;

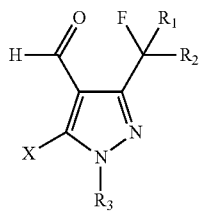

Equation I

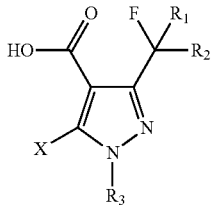

Equation II

Where, $R_1$ and $R_2$ are hydrogen or fluorine atom; $R_3$ is hydrogen atom or lower paraffin hydrocarbon of $C_1$-$C_4$ and X is hydrogen or helium atom.

In the process of reaction, nanometer copper oxide is adopted as the catalyst, of which the weight ratio to 3-fluoroalkyl-1-substituted pyrazol-4-formaldehyde is 0.001-0.1:1; the reaction temperature is controlled in the range of 25° C.-50° C.

The said alkaline environment can be realized by adding sodium hydroxide, potassium hydroxide or lithium hydrate.

The beneficial effects of the Invention are that the method employs a mild, safe and clean reaction, and is suitable for industrial mass production.

DETAILED DESCRIPTION OF THE PREFERRED EMBODIMENTS

The followings are detailed embodiments of the Invention, of which Embodiments 1-3 are for preparing 3-difluoromethyl-1-methyl-5-chloropyrazole-4-formic acid, Embodiment 4 is for preparing 3-difluoromethyl-1-methylpyrazole-4-formic acid, Embodiment 5 is for preparing 3-difluoromethyl pyrazole-4-formic acid and Embodiment 6 is for preparing 3-trifluoromethyl-1-methyl-5-chloropyrazole-4-formic acid, to which the Invention is not limited, however.

Embodiment 1

Add and stir 38.9g of 3-difluoromethyl-1-methyl-5-chloropyrazole-4-formaldehyde, 390 ml of water and 8.4 g of sodium hydroxide in a reaction flask of 1000 mL. Then add 1 g of nanometer copper oxide and control the reaction temperature at 25-30° C. Introduce the air for oxidation reaction for 15 hours so that the amount of HPLC raw material, i.e. 3-difluoromethyl-1-methyl-5-chloropyrazole-4-formaldehyde, is less than 0.2% of the total amount; stop the reaction, filtrate and recycle the copper catalyst. Cool the reaction solution to 10° C. or below and add 31% hydrochloric acid to get the pH value of 1-2; precipitate a solid and filtrate; wash the solid with a little water and dry to get 40 g of the product, i.e. 3-difluoromethyl-1-methyl-5-chloropyrazole-4-formic acid. HPLC content is 99%; LC-MS: m/e=210.

Embodiment 2

Add and stir 38.9 g of 3-difluoromethyl-1-methyl-5-chloropyrazole-4-formaldehyde, 390 ml of water and 12.6 g of lithium hydroxide monohydrate in a reaction flask of 1000 mL. Then add 2 g of nanometer copper oxide and control the reaction temperature at 40-50° C. Introduce the air for oxidation reaction for 15 hours so that the amount of HPLC raw material, i.e. 3-difluoromethyl-1-methyl-5-chloropyrazole-4-formaldehyde, is less than 0.2% of the total amount; stop the reaction, filtrate and recycle the copper catalyst. Cool the reaction solution to 10° C. or below and add 31% hydrochloric acid to get the pH value of 1-2; precipitate the solid and filtrate; wash the solid with a little water and dry to get 40 g of the product, i.e. 3-difluoromethyl-1-methyl-5-chloropyrazole-4-formic acid. HPLC content is 95%, containing a little 3-difluoromethyl-1-methyl-5-chloropyrazole-4-methyl alcohol; LC-MS: m/e=210.

Embodiment 3

Add and stir 38.9 g of 3-difluoromethyl-1-methyl-5-chloropyrazole-4-formaldehyde, 390 ml of water and 9.1 g 90% potassium hydroxide in a reaction flask of 1000 mL. Then add 0.8 g of nanometer copper oxide and control the reaction temperature at 25-30° C. Introduce the air for oxidation reaction for 24 hours so that the amount of HPLC raw material, i.e. 3-difluoromethyl-1-methyl-5-chloropyrazole-4-formaldehyde, is less than 0.2% of the total amount; stop the reaction, filtrate and recycle the copper catalyst. Cool the reaction solution to 10° C. or below and add 31% hydrochloric acid to get the pH value of 1-2; precipitate the solid and filtrate; wash the solid with a little water and dry to get 40 g of the product, i.e. 3-difluoromethyl-1-methyl-5-chloropyrazole-4-formic acid. HPLC content is 99%; LC-MS: m/e=210.

Embodiment 4

Add and stir 32 g of 3-difluoromethyl-1-methylpyrazol-4-formaldehyde, 390 ml of water and 8.4 g of sodium hydroxide in a reaction flask of 1000 mL. Then add 2 g of nanometer copper oxide and control the reaction temperature at 25-30° C. Introduce the air for oxidation reaction for 24 hours so that the amount of HPLC raw material, i.e. 3-difluoromethyl-1-methylpyrazol-4-formaldehyde, is less than 0.2% of the total amount; stop the reaction, filtrate and recycle the copper catalyst. Cool the reaction solution to 10° C. or below and add 31% hydrochloric acid to get the pH value of 1-2; precipitate the solid and filtrate; wash the solid with a little water and dry to get 32 g of the product, i.e. 3-difluoromethyl-1-methylpyrazol-4-formic acid. HPLC content is 99%; LC-MS: m/e=176.

Embodiment 5

Add and stir 29.2 g of 3-difluoromethyl pyrazole-4-formaldehyde and 58.4 ml of water in a reaction flask of 1000mL. Then add 2 g of nanometer copper oxide and control the reaction temperature at 25-30° C. Introduce the air for oxidation reaction for 48 hours so that the amount of HPLC raw material, i.e. 3-difluoromethyl pyrazole-4-formaldehyde, is less than 1% of the total amount; stop the reaction, filtrate and obtain the raw product (containing copper catalyst); dissolve the solid dichloromethane; filtrate and recycle the copper catalyst. Concentrate the filtrate to obtain 30 g of the product, i.e. 3-difluoromethyl pyrazole-4-formic acid. HPLC content is 98%; LC-MS: m/e=162.

Embodiment 6

Add and stir 42.5 g of 3-trifluoromethyl-1-methyl-5-chloropyrazole-4-formaldehyde, 425 ml of water and 8.4g of sodium hydroxide in a reaction flask of 1000 mL. Then add 4.2 g of nanometer copper oxide and control the reaction temperature at 25-30° C. Introduce the air for oxidation reaction for 15 hours so that the amount of HPLC raw material, i.e. 3-difluoromethyl-1-methyl-5-chloropyrazole-4-formaldehyde, is less than 0.2% of the total amount; stop the reaction, filtrate and recycle the copper catalyst. Cool the reaction solution to 10° C. or below and add 31% hydrochloric acid to get the pH value of 1-2; precipitate the solid and filtrate; wash the solid with a little water and dry to get 43 g of the product, i.e. 3-trifluoromethyl-1-methyl-5-chloropyrazole-4-formic acid. HPLC content is 99%; LC-MS: m/e=228.

What is claimed is:

1. A method of preparing 3-fluoroalkyl-1-substituted pyrazol-4-carboxylic acid by air oxidation, wherein 3-fluoroalkyl-1-substituted pyrazol-4-carboxylic acid (Equation II) is obtained with 3-fluoroalkyl-1-substituted pyrazol-4-formaldehyde (Equation I) as raw material for reaction in a neutral or alkaline condition under the action of a catalyst and with the air as an oxidizing agent;

Equation I

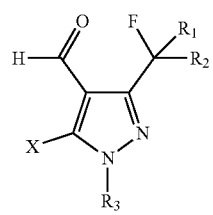

Equation II

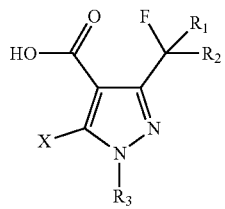

where, R1 and R2 are hydrogen or fluorine atom; R3 is hydrogen atom or lower paraffin hydrocarbon of $C_1$-$C_4$ and X is hydrogen or helium atom; wherein said catalyst is nanometer copper oxide.

2. A method of preparing 3-fluoroalkyl-1-substituted pyrazol-4-carboxylic acid by air oxidation according to claim 1 wherein the weight ratio of the said catalyst to the 3-fluoroalkyl-1-substituted pyrazol-4-formaldehyde is 0.001-0.1:1.

3. A method of preparing 3-fluoroalkyl-1-substituted pyrazol-4-carboxylic acid by air oxidation according to claim 1, wherein the said alkaline environment is realized by adding sodium hydroxide, potassium hydroxide or lithium hydrate.

4. A method of preparing 3-fluoroalkyl-1-substituted pyrazol-4-carboxylic acid by air oxidation according to claim 1, wherein the temperature is controlled in the range of 25° C.-50° C. in the process of reaction.

* * * * *